United States Patent [19]

Bartl et al.

[11] 4,234,682

[45] Nov. 18, 1980

[54] METHOD AND REAGENT FOR DETERMINING BIOLOGICALLY ACTIVE HEPARIN IN PLASMA

[75] Inventors: Knut Bartl, Tutzing; Helmut Lill, Wielenbach; Joachim Ziegenhorn, Starnberg, all of Fed. Rep. of Germany

[73] Assignee: Boehringer Mannheim GmbH, Mannheim-Waldhof, Fed. Rep. of Germany

[21] Appl. No.: 13,759

[22] Filed: Feb. 21, 1979

[30] Foreign Application Priority Data

Mar. 23, 1978 [DE] Fed. Rep. of Germany ....... 2812943

[51] Int. Cl.³ .......................... C12Q 1/38; C12Q 1/56
[52] U.S. Cl. ......................................... 435/13; 435/23
[58] Field of Search ................................. 435/13, 23; 195/103.5 R, 99

[56] References Cited

U.S. PATENT DOCUMENTS

| | | | |
|---|---|---|---|
| 3,884,896 | 5/1975 | Blomback et al. | 435/13 X |
| 4,061,625 | 12/1977 | Ekenstam et al. | 435/13 X |
| 4,067,777 | 1/1978 | Innerfield et al. | 435/13 |
| 4,070,245 | 1/1978 | Svendsen | 435/13 |
| 4,106,990 | 8/1978 | Karges et al. | 435/13 |
| 4,162,941 | 7/1979 | Aurell et al. | 435/23 |

OTHER PUBLICATIONS

Witt, *J. Clin. Chem. Clin. Biochem.,* 15, 239–244 (1977).
Teien et al, Chemical Abstracts 86:27402v (1976), p. 164.

*Primary Examiner*—Esther M. Kepplinger
*Attorney, Agent, or Firm*—Sprung, Felfe, Horn, Lynch & Kramer

[57] ABSTRACT

A method for determining biologically active heparin comprising adding, in the absence of exogenous antithrombin III, a proteolytic enzyme selected from the group consisting of thrombin and factor Xa and a chromogen substrate for the enzyme to a heparin sample, measuring the dye released from the chromogen substrate and thus determining the amount of heparin present.

7 Claims, 1 Drawing Figure

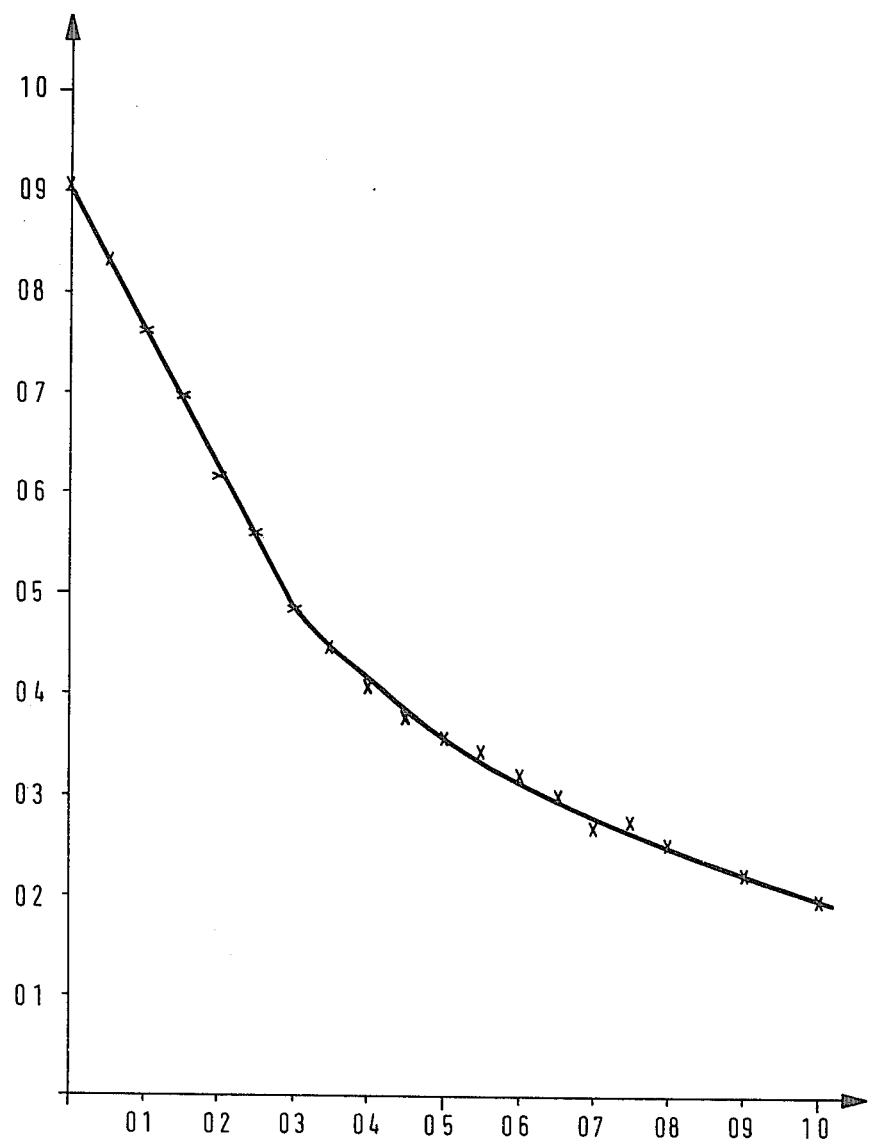

METHOD AND REAGENT FOR DETERMINING BIOLOGICALLY ACTIVE HEPARIN IN PLASMA

The invention relates to a method and a reagent for the determination of biologically active heparin in plasma.

The determination of heparin establishes an important parameter for the supervision of heparin treatment which is often administered in the presence of a threat of thrombosis. Heparin forms with antithrombin III (AT III) a complex which inhibits the proteolytic activity of thrombin. Since thrombin catalyzes the formation of fibrin from fibrinogen, the thrombin activity is responsible for the coagulation of blood or plasma and hence also for the fibrin clots which form in thrombosis. Heparin treatment is often applied in the presence of a threat of thrombosis (e.g., before surgical interventions). A precise adjustment of the heparin concentration is then extremely important. If the dose is too low, there is the danger of thrombosis or embolism, which can result in death. Excessively high heparin concentrations, however, result in bleeding. The quantitative analysis of heparin, therefore, is one of the tests most frequently performed in the blood testing laboratory.

Basically, two methods have been used hitherto in the determination of heparin:

1. Determination of the clotting activity of blood or plasma. The methods based hereon, however, are unsatisfactory. Particularly in the low concentration range the sensitivity is too low, but high concentrations result in noncoagulability making the test impossible to perform (cf. Thromb. Res. 8, 413, [1976]).
2. More recently, the use of chromogenic substrates for the Xa enzyme factor or thrombin (J. Clin. Chem. Clin. Biochem. 15, 239 [1977]).

This newer method is based on the following principle:

The plasma sample containing the heparin as well as an unknown, varying amount of antithrombin III (AT III or heparin cofactor) is incubated with factor Xa or thrombin in the presence of added AT III. The added AT III is intended on the one hand to compensate the varying amounts of AT III in the sample by creating an excess, and on the other hand it is needed in order to increase sufficiently the sensitivity of the test, especially in the low range of heparin concentration. The AT III can be added either in the form of normal plasma, which always contains physiological amounts of AT III, or in the form of purified AT III. During this incubation, the heparin contained in the sample produces by catalysis a change in the conformation of the AT III resulting in its activation. The activated AT III is then capable of spontaneously inactivating a portion of the proteolytic enzyme Xa or thrombin contained in the incubation solution by forming a covalent bond. The proteolytic enzyme which is not inhibited by heparin-activated AT III can then liberate from a suitable chromogenic substrate, as a rule a peptide containing p-nitroaniline, such as Bz-Ile-Glu-Gly-Arg-pNA or Tos-Gly-Pro-Arg-pNA, the dye p-nitroaniline whose extinction can be measured at 405 nm. The difference between the enzyme activity use ($E_1$/min) and the residual activity ($E_2$/min) is compared through a calibration curve with the heparin concentration in the sample. The following reaction equations explain this process:

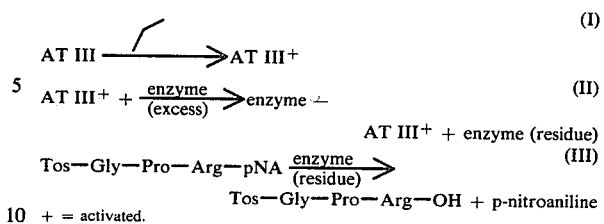

$+$ = activated.

By the addition of an excess of AT III in the form of normal plasma or in the form of purified AT III, the determination of heparin by this method is largely independent of the AT III in the plasma sample. One determines, therefore all of the heparin contained in the sample that is capable through AT III of inactivating thrombin or factor Xa. It has been found, however, that this system has the following disadvantages: An AT III deficiency frequently occurring in patient plasmas cannot be recognized on account of the added AT III. In the extreme case, and one that is actually encountered in clinical practice, the patient has virtually no At III, and heparin therapy alone would be ineffective. Heparin would exercise no biological activity whatever on thrombin. The physician has been obtaining on the basis of this test principle a falsified picture of the coagulation conditions in the patient. As a result, a determination of AT III must be performed in addition to the heparin determination.

The invention provides a method for the direct determination of the biological activity of heparin.

The method of the invention for determining biologically active heparin comprises essentially adding a proteolytic enzyme and a chromogen substrate of the latter to the heparin sample, measuring the dye released from the chromogen substrate and making the determination in the absence of added antithrombin III; the proteolytic enzyme used is thrombin or factor Xa.

According to information in the literature, it is not until purified AT III is added that the sensitivity of the heparin determination is increased to the degree that even small amounts of heparin (down to 10 U/l) can be determined.

Surprisingly, however, it is possible by the method of the invention to measure plasma in the low concentration range containing normal amounts of AT III, and to do so with sufficient sensitivity, even without the addition of AT III. For example, in the performance of the test at 37° C., 20 USP per liter of plasma can be tested with sufficient accuracy. Since external AT III is no longer used in the test, both of the parameters heparin and AT III are tested in accordance with the biological mechanism of thrombin inactivation. This is because by means of the AT III obtained in the sample, the heparin which is to be determined in the specimen is able to exercise its biological activity in the form of inactivation of thrombin. This method provides the physician with direct supervision of the coagulating capacity of the blood of a patient in heparin therapy.

Chromogenic substrates for the proteolytic enzyme are to be understood in general to be substrates which under the action of the enzyme release a dye. This can be a dye that can be determined in the visible range of the spectrum, a fluorescent dye, or a dye which can be determined in the ultraviolet range. Preferred as chromogenic substrates are peptides having a dye moiety bound by an amide bond to the carboxyl group of an arginine moiety. Particularly suitable for this purpose is the p-nitroanilide moiety, as well as similar dyes derived therefrom by substitution. But other dyes containing amino groups can be bonded to the carboxyl group of the arginine moiety.

If thrombin is used the preferred substrates are Bz-Phe-Val-Arg-pNA, H-D-Phe-Pip-Arg-pNA or Tos-Gly-Pro-Arg-pNA.

If factor Xa is used, Bz-Ile-Glu-Gly-Arg-pNA is preferred for use as the chromogenic substrate.

The process conditions with regard to pH, time, temperature and the like are substantially the same as those of the known method. It is preferable to operate with a pH of 8.0 and with tris-(hydroxymethyl)-aminomethane/HCl buffer. Other buffering systems, such as tris-(hydroxymethyl)-amino-methane/imidazole buffer or imidazole/HCl buffer, however, are also usable. The determination is best performed at room temperature, but it can also be performed at higher temperatures (30° to 37° C.), in which case lower enzyme concentrations are used, corresponding to a higher thrombin activity.

To obtain an optimum ion strength in the test mixture, salts are added to the buffer solution, preferably alkali chlorides such as NaCl or KCl. It is preferable to add aprotinin to inhibit undesired activities in the test plasma.

Additional subject matter of the invention is a reagent for determining heparin in plasma, which consists essentially of:
0.01 to 0.3 moles/l of buffer, pH 6 to 9,
0.01 to 0.25 moles/l of alkali chloride,
200 to 1100 NIH/l of thrombin or factor Xa,
0.05 to 10 mmoles/l of chromogenic substrate,
0 to 0.01 g/l of aprotinin,
0 to 0.03 moles/l of EDTA, and
0 to 10 g/l of polyethylene glycol.

The method and reagent of the invention is distinguished by the fact that one component less is required for the performance of the test than in the known methods. Consequently the manual test acquires practicability. Mainly, however, this method is better suited for adaptation to automatic analysis apparatus. In addition, the omission of the additional AT III is extremely beneficial as regards the cost per test batch, because the availability both of normal plasma and of purified AT III constitutes a limiting factor. Nevertheless the important advantage of the method can be said to be the better information which it gives to the user in clinical practice.

The process can be performed kinetically, in which case the speed of the reactions of the initial thrombin activity and of the thrombin residual activity immediately after the start of the reaction with the substrate serves as a parameter. Furthermore, the end-value method can also be used, in which the reaction is stopped by alteration of the pH with acids, such as acetic acid, for example, after a certain length of time.

The test mixture contains:
0.045 moles/l of tris/HCl buffer, pH 8.0,
0.14 moles/l of NaCl,
0.01 moles/l of EDTA (ethylenediamine tetraacetic acid),
9 g/l of polyethylene glycol,
0.01 g/l of aprotinin,
300 NIH/l of thrombin,
0.14 mmol/l of Tos-Gly-Pro-Arg-pNA.

EXAMPLE

The example described below was performed by the kinetic method using the following reagents:

Reagent 1:
0.05 mol/l of tris/HCl buffer, pH 8.0
0.15 mol/l of Nacl,
0.01 mol/l of EDTA,
10 g/l of polyethyleneglycol,
0.01 g/l of aprotinin
330 NIH/l of thrombin.

Reagent 2:
1.5 mmol/l of Tos-Gly-Pro-Arg-pNA

Determination Mixture:
Measuring radiation: Hg 405 nm; depth of liquid in the cell: 1 cm,
Incubation temperature: room temperature.
Pipette 2.0 ml of reagent 1 into the cell, add 0.02 ml of sample, and mix. Incubate 3 minutes at 25° C., then admix 0.2 ml of reagent 2. Record extinction 3 minutes at 25° C.

A blank value is to be determined for each series of measurements, using water instead of the test plasma.

Evaluation: Find the difference between the extinction change per 3 minutes for the blank value and the extinction change per 3 minutes for the sample. This difference is a measure of the biological activity of the heparin in the plasma. The absolute extinction after 3 minutes can also be used for the evaluation, as represented in FIG. 1. This FIG. 1 shows the results for 18 plasma samples to which weighed amounts of heparin were added to produce a concentration range from 0.05 to 1.0 USP of heparin per milliter of plasma.

The reagent contains approximately:
0.01 to 0.3 mol/l of buffer, pH 6 to 9,
0.01 to 0.25 mol/l of NaCl,
0.001 to 0.03 mol/l of EDTA,
200 to 1100 NIH/l of thrombin, $\geq 0.05$ mmol/l of substrate,
0 to 0.01 g/l of aprotinin and
0 to 10 g/l of polyethyleneglycol.

It will be understood that the specification and examples are illustrative, but not limitative of the present invention and that other embodiments within the spirit and scope of the invention will suggest themselves to those skilled in the art.

What is claimed is:

1. Method for the determination of the biological activity of heparin in plasma which method comprises adding to the heparin sample a proteolytic enzyme selected from thrombin or factor Xa, and a chromogen substrate of said proteolytic enzyme, without addition of exogenous antithrombin III, and measuring the dye released from the chromogen substrate as a measure of the heparin activity initially present.

2. Method as claimed in claim 1 wherein said chromogen substrate is a peptide having a p-nitroanilide moiety bound, via amide bonding, to the carboxyl group of an arginine moiety.

3. Method as claimed in claim 1 wherein said proteolytic enzyme is thrombin and said chromogen substrate is selected from Bz-Phe-Val-Arg-pNA, H-D-Phe-Pip-Arg-pNA and Tos-Gly-Pro-Arg-pNA.

4. Method as claimed in claim 1 wherein the proteolytic enzyme is factor Xa and said chromogen substrate is Bz-ILe-Glu-Gly-Arg-pNA.

5. Method as claimed in claim 1 wherein aprotinin is additionally added in said determination.

6. Reagent for the determination of heparin in plasma consisting essentially of
   0.01 to 0.3 moles/l of buffer, pH 6 to 9
   0.01 to 0.25 moles/l of alkali chloride,
   200 to 1100 NIH/l of thrombin
   0.05 to 10 mmoles/l of chromogen substrate for thrombin,
   0 to 0.01 g/l of aprotinin,
   0 to 10 g/l of polyethylene glycol.
   0 to 0.03 moles/l EDTA 7. Reagent for the determination of heparin in plasma consisting essentially of
   0.01 to 0.3 moles/l of buffer, pH 6 to 9
   0.01 to 0.25 moles/l of alkali chloride,
   200 to 1100 NIH/l of factor Xa,
   0.05 to 10 mmoles/l of chromogen substrate for factor Xa,
   0 to 0.01 g/l of aprotinin,
   0 to 10 g/l of polyethylene glycol.
   0 to 0.03 moles/l EDTA

* * * * *